United States Patent [19]

Deschamps et al.

[11] Patent Number: 4,505,880
[45] Date of Patent: Mar. 19, 1985

[54] PROCESS FOR THE HYDRODESULFURIZATION AND DEOXYGENATION OF A GAS CONTAINING OXYGEN AND ORGANIC SULFUR COMPOUNDS

[75] Inventors: André Deschamps, Noisy le Roi; Jean Cosyns, Maule; Jean-Francois Le Page; Gérard Hotier, both of Rueil-Malmaison, all of France

[73] Assignee: Institut Francais du Petrole, Rueil-Malmaison, France

[21] Appl. No.: 466,689

[22] Filed: Feb. 15, 1983

[30] Foreign Application Priority Data

May 25, 1982 [FR] France .................. 82 09210

[51] Int. Cl.$^3$ .................................................. B01D 53/56
[52] U.S. Cl. ...................... 423/219; 423/230; 423/244; 423/245; 423/563
[58] Field of Search ............... 423/210, 219, 224, 230, 423/244, 245, 563, 564; 502/262, 333

[56] References Cited

U.S. PATENT DOCUMENTS

| | | | |
|---|---|---|---|
| 3,420,618 | 1/1969 | Fleming | 423/219 |
| 4,175,928 | 11/1979 | Britton et al. | 423/230 |
| 4,181,503 | 1/1980 | Lesieur et al. | 423/650 X |
| 4,460,553 | 7/1984 | Deschamps et al. | 423/219 |

FOREIGN PATENT DOCUMENTS

| | | | |
|---|---|---|---|
| 2521448 | 8/1983 | France | 423/219 |
| 340016 | 12/1930 | United Kingdom | 423/244 R |

Primary Examiner—Earl C. Thomas
Attorney, Agent, or Firm—Millen & White

[57] ABSTRACT

Process for hydrodesulfurizing and deoxygenating a gas (A) comprising methane, oxygen and at least one organic sulfur compound, said process comprising contacting a mixture of said gas (A) with a hydrogen-containing gas (B) first with a palladium-containing catalyst, at a temperature of 300°–450° C., and then with a second catalyst comprising molybdenum and at least one of nickel and cobalt, at a temperature of 300°–450° C.

12 Claims, No Drawings

PROCESS FOR THE HYDRODESULFURIZATION AND DEOXYGENATION OF A GAS CONTAINING OXYGEN AND ORGANIC SULFUR COMPOUNDS

BACKGROUND OF THE INVENTION

The invention relates to a process for the hydrodesulfurization and deoxygenation of a gas simultaneously comprising oxygen and organic sulfur compounds.

Natural gas, as distributed by pipe network, contains traces of organic sulfur compounds resulting from an incomplete desulfurization or voluntarily introduced to give a smell to the gas (usually tetrahydrothiophene (THT) or mercaptans). Although present in the gas at a low concentration (for example 10 to 30 mg THT per Normal cubic meter of gas), these sulfur compounds are a nuisance when the gas is used in the presence of sulfur-sensitive catalysts. It is especially the case when the gas is used to manufacture hydrogen or synthesis gas by stream reforming, for example in ammonia or methanol producing plants.

The gas is usually desulfurized by hydrogen treatment in the presence of a hydrodesulfurization catalyst to convert the organic sulfur compounds to hydrogen sulfide which can be easily separated or retained by, for example, a zinc oxide mass. The catalysts to be used in the hydrodesulfurization step usually comprise cobalt and molybdenum or nickel and molybdenum on an alumina carrier.

The network gas sometimes also contains small amounts of air added to adjust the combustion power of too rich gases. The oxygen content is usually from 0.05 to 1% by volume. The hydrodesulfurization catalysts do not work properly in these conditions: a portion of sulfur is converted to elemental sulfur and/or sulfur dioxide which are not retained by the zinc oxide mass and poison the catalysts used in the subsequent treatment of the gas.

Other gases containing both oxygen and organic sulfur compounds (for example COS, $CS_2$, mercaptans, sulfides, disulfides) are, for example, obtained by coking and gasification of coal, lignite, bituminous shales or oil residues, or consist of the associated gases of oil wells or refinery gases.

Two methods have been proposed to obviate this disadvantage.

According to U.S. Pat. No. 4,181,503, oxygen is removed in a first step by treatment of a mixture of the gas with hydrogen on a platinum-containing catalyst; then, in a second step, the oxygen-free gas is treated on a nickel-molybdenum catalyst to convert organic sulfur to hydrogen sulfide. This process has the disadvantage of being costly since, on the one hand, it requires a platinum catalyst and, on the other hand, the successive passage of the two catalysts cannot always be performed inside an already existing reactor only designed for the hydrodesulfurization of an oxygen-free gas.

The French patent application No. 82 02 550, now French Pat. No. 2,521,448, discloses the simultaneous performance of these two operations by treatment of the gas, after hydrogen addition (or more advantageously addition of an industrial gas comprising both hydrogen and carbon monoxide), on a palladium-containing catalyst.

SUMMARY OF THE INVENTION

It has now been discovered, and this is the object of the invention, that the association of a palladium-containing catalyst with a conventional hydrodesulfurization catalyst containing molybdenum and nickel and/or cobalt performs the deoxygenation and the hydrodesulfurization under particularly advantageous conditions.

DETAILED DISCUSSION

According to a particular embodiment of the invention, a gas containing more than 2 $mg/Nm^3$, for example 2 to 20 $mg/Nm^3$, particularly 4 to 12 $mg/Nm^3$ of sulfur as organic sulfur compounds and 0.05 to 2% by volume, more particularly 0.1 to 1% by volume, of oxygen, is treated with a hydrogen-containing gas at a temperature of 300° to 450° C., preferably 320° to 400° C., first in the presence of a palladium catalyst and then in the presence of a cobalt-molybdenum and/or nickel-molybdenum catalyst.

The first (palladium) catalyst represents, by volume, 20 to 60%, preferably 30 to 50%, of the total volume of the catalysts, the second catalyst representing respectively 40 to 80%, preferably 50 to 70% of this total volume.

The two catalysts are preferably placed in the same reactor, which represents a substantial saving in investment and operating cost.

The hydrogenation gas can be relatively pure hydrogen or more advantageously an industrial gas containing both hydrogen and carbon monoxide.

The first catalyst consists of 0.1 to 5% b.w. of palladium deposited on (or incorporated into) a carrier such as, for example, alumina, silica or silica-alumina, the specific surface of the carrier (BET method) being preferably from 5 to 400 $m^2/g$. Any appropriate method can be used to incorporate palladium, such as: impregnation with an aqueous solution of a palladium compound, for example an aqueous solution of a nitrate, a chloride or an amine complex of the Pd $(NH_3)_4X_2$ type (X being an anion) or a solution of an organic complex such as palladium acetylacetonate dissolved in an appropriate organic compound.

After impregnation, the palladium compound is treated in any appropriate manner to obtain the reduced metal, for example by calcination in the air followed with hydrogen reduction. Prior to its use, the catalyst can also be treated with a mixture of hydrogen and a sulfur compound such as, for example, $H_2S$.

The nickel-molybdenum or cobalt-molybdenum catalysts are well known and need not to be described in detail. They comprise usually 5 to 30% b.w. of molybdenum, calculated as $MoO_3$, and 1 to 10% b.w. of nickel and/or cobalt, calculated as NiO or CoO, the remainder being a carrier, for example alumina, silica or silica-alumina of specific surface between 50 and 400 $m^2/g$. Alumina is preferred.

The space velocity, i.e. the gas volume (under normal conditions of temperature and pressure) per volume of catalyst and per hour is from 1,000 to 25,000 and more specially from 4,000 to 16,000 for each catalyst considered separately.

The hydrogen amount is at least the stoichiometrical amount required to convert the organic sulfur compounds to hydrogen sulfide and to convert oxygen to steam. It is preferably at least twice this amount, usually from 2 to 6% by volume of the natural gas amount.

The operating pressure may vary widely, for example from 1 to 80 bars. The preferred pressure is the network pressure or the pressure at which the gas is utilized, i.e. usually 20 to 60 bars.

The organic sulfur compounds to be eliminated by the process of the invention are, for example:
tetrahydrothiophene,
mercaptans of the formula R—SH where R=hydrocarbyl of 1–6 carbon atoms, for example methylmercaptan, ethylmercaptan, propylmercaptans and butylmercaptans,
sulfides of the formula $R_1R_2S$ where $R_1$ and $R_2$ are each hydrocarbyl of 1–4 carbon atoms, for example methyl sulfide, ethyl sulfide and butyl sulfide,
disulfides of the formula $R_1SSR_2$ where $R_1$ and $R_2$ are each hydrocarbyl of 1–4 carbon atoms, for example dimethyldisulfide, diethyldisulfide and dipropyldisulfide.

EXAMPLE

The performances of catalysts of the trade comprising respectively nickel and molybdenum (14% $MoO_3$+3% NiO by weight) on alumina and cobalt and molybdenum (14% $MoO_3$+3% CoO by weight) on alumina have been compared to those obtained with a palladium on alumina catalyst (0.3% Pd by weight) employed either alone or followed with a catalyst of the trade comprising nickel and molybdenum (14% $MoO_3$+3% NiO) on alumina of a specific surface of 150 $m^2/g$ or with a catalyst of the trade comprising cobalt and molybdenum (14% $MoO_3$+3% CoO).

The palladium catalyst was prepared as follows: an alumina carrier having a specific surface of 70 $m^2/g$ and a pore volume of 0.6 cc/g was impregnated with a palladium nitrate solution, so as to obtain 0.3% b.w. of palladium metal in the final catalyst. After impregnation, the catalyst was dried and then calcined at 450° C. for 2 hours in an air stream. Before use, the catalyst was reduced at 200° C. in a hydrogen stream for 2 hours.

The gas to be treated was natural gas consisting essentially of methane and comprising 25 mg/$Nm^3$ of tetrahydrothiophene (THT) and 0.5% by volume of oxygen.

An electrically heated tubular steel reactor of 3 cm internal diameter was charged with respectively:
100 cc of CoMo catalyst
or 100 cc of NiMo catalyst
or 100 cc of palladium catalyst
or 50 cc of palladium catalyst followed (downstream) with either 50 cc of NiMo catalyst or 50 cc of CoMo catalyst.

500N l/h of natural gas and 15N l/h of hydrogen were introduced at the top of the reactor under a 30 bar pressure.

The gas discharged from the bottom of the reactor was expanded and analysed to determine the contents of THT, $H_2S$, elemental sulfur, $SO_2$, organic sulfur and oxygen.

The following Table gives the results obtained with each catalyst, at different temperatures, after a 100 hour starting period.

It is found that the palladium catalyst, when used alone or in association with the NiMo and CoMo catalysts, gives an almost complete conversion of THT in the temperature interval of 300° to 400° C., particularly 350° to 400° C. As concerns the palladium catalyst, when used alone, traces of organic sulfur are observed, which may be a nuisance; conversely when the palladium catalyst and the NiMo or CoMo catalysts are associated, these traces of organic sulfur compounds are no longer present.

Conversely, the cobalt-molybdenum or nickel molybdenum catalyst gives at any temperature a gas comprising, in addition to traces of hydrogen sulfide, sulfur dioxide and elemental sulfur. This appears to result from the permanent presence of oxygen in the effluent gas. Moreover, at each temperature increase, the sulfur dioxide content temporarily increases, probably as a result of the oxidation of cobalt (or nickel) and molybdenum sulfides present in the catalyst.

It has also been found that the presence of $CO_2$ in the gas to be treated did not result in methanation and that the higher hydrocarbons such as ethane, propane and butanes were not subject to hydrogenolysis. Excessive hydrogen consumptions as a result of such reactions are thus not liable to occur.

| CATALYST | T °C. | THT mg/$Nm^3$ | $H_2S$ mg/$Nm^3$ | ELEMENTAL SULFUR mg/$Nm^3$ | $SO_2$ mg/$Nm^3$ | TOTAL ORGANIC SULFUR mg/$Nm^3$ | $O_2$ ppm vol. |
|---|---|---|---|---|---|---|---|
| Pd/$Al_2O_3$ | 300 | <0.05 | 9 | 0.1 | 1 | 0.4 | 15 |
|  | 350 | <0.05 | 9.35 | nd | nd | 0.3 | nd |
|  | 400 | <0.05 | 9.53 | nd | nd | 0.1 | nd |
| Pd/$Al_2O_3$ 50% NiMo/$Al_2O_3$ 50% | 300 | <0.05 | 9 | nd | nd | 0.2 | 15 |
|  | 350 | <0.05 | 9.60 | nd | nd | <0.1 | nd |
|  | 400 | <0.05 | 9.62 | nd | nd | <0.1 | nd |
| NiMo/$Al_2O_3$ | 300 | 6 | 4 | 2 | 8 | 6 | 4300 |
|  | 350 | <0.05 | 2 | 1 | 12 | 2 | 4000 |
|  | 400 | <0.05 | 1 | 0.5 | 14 | 2.7 | 700 |
| Pd/$Al_2O_3$ 50% CoMo/$Al_2O_3$ 50% | 300 | <0.05 | 9.1 | nd | nd | 0.25 | 20 |
|  | 350 | <0.05 | 9.55 | nd | nd | <0.1 | 10 |
|  | 400 | <0.05 | 9.65 | nd | nd | <0.1 | nd |
| CoMo/$Al_2O_3$ | 300 | 5 | 3 | 1.5 | 6.5 | 9 | 4500 |
|  | 350 | <0.05 | 1 | 0.5 | 14.1 | 4.4 | 4100 |
|  | 400 | <0.05 | 2 | 1 | 13 | 3.7 | 1000 | nd: not detected

What is claimed is:

1. A process for hydrodesulfurizing and deoxygenating a gas (A) comprising methane, oxygen and at least one organic sulfur compound, said process comprising contacting a mixture of said gas (A) with a hydrogen-containing gas (B) first with a palladium-containing catalyst, at a temperature of 300°–450° C., and then with a second catalyst comprising molybdenum and at least one of nickel and cobalt, at a temperature of 300°–450° C.; wherein said contacting is effected at a space velocity of 1,000–25,000 with respect to each said catalyst.

2. A process according to claim 1, wherein the gas (A) comprises at least 2 mg of sulfur, as organic sulfur compound, per $Nm^3$ and 0.05 to 2% by volume of oxygen.

3. A process according to claim 2, wherein the gas (A) comprises 2 to 20 mg of sulfur, as organic sulfur compound, per $Nm^3$.

4. A process according to claim 1, wherein the temperature is from 320° to 400° C.

5. A process according to claim 1, wherein the hydrogen proportion is at least the theoretical proportion necessary for the conversion of the organic sulfur compound to hydrogen sulfide and for the conversion of oxygen to steam.

6. A process according to claim 1, wherein the hydrogen amount represents 2 to 6% by volume of the gas (A).

7. A process according to claim 1, wherein the first catalyst comprises 0.1 to 5% by weight of palladium on alumina or silica, and the second catalyst comprises 5 to 30% by weight of molybdenum, calculated as $MoO_3$, and 1 to 10% by weight of nickel and/or cobalt, calculated as NiO and/or CoO, on alumina, silica or silica-alumina.

8. A process according to claim 1, wherein the first catalyst and the second catalyst represent respectively 20 to 60% and 80 to 40% of the total volume of the catalysts.

9. A process according to claim 1, wherein the first catalyst and the second catalyst are in the same reaction zone.

10. A process according to claim 1, wherein said space velocity is 4,000–16,000.

11. A process according to claim 2, wherein said gas (A) contains 4–12 $mg/Nm^3$ of sulfur, as organic sulfur compound, and 0.1–1% by volume of oxygen.

12. A process according to claim 8, wherein the first catalyst and the second catalyst represent respectively 30–50% and 50–70% of the total volume of the catalysts.

* * * * *